United States Patent [19]

Nishizawa et al.

[11] Patent Number: 5,052,818
[45] Date of Patent: Oct. 1, 1991

[54] METHOD OF AND APPARATUS FOR MEASURING VERY LOW WATER CONTENT IN GAS

[75] Inventors: Junichi Nishizawa, Miyagi; Taichi Tagawa, Shiga; Takahiko Kijima, Osaka, all of Japan

[73] Assignees: Junichi Nishizawa, Miyagi; Osaka Sanso Kogyo Ltd., Osaka, both of Japan

[21] Appl. No.: 353,429

[22] Filed: May 18, 1989

Related U.S. Application Data

[63] Continuation-in-part of Ser. No. 202,744, Jun. 6, 1988.

[30] Foreign Application Priority Data

Jun. 11, 1987 [JP] Japan ............................ 62-145764

[51] Int. Cl.$^5$ ...................... G01N 25/68; G01N 21/47
[52] U.S. Cl. ...................... 374/17; 73/336.5; 374/20
[58] Field of Search ................. 374/18, 19, 20, 28, 374/27, 25, 16, 17; 73/29, 335, 336.5; 356/446; 340/601, 602

[56] References Cited

U.S. PATENT DOCUMENTS

| | | | |
|---|---|---|---|
| 3,269,185 | 1/1963 | Francisco | 374/19 |
| 3,281,814 | 10/1966 | Munchen | 374/20 |
| 3,943,774 | 3/1976 | Pollanz | 73/1 R |
| 4,083,224 | 4/1978 | Gayst | 374/19 |
| 4,083,249 | 4/1978 | Gerber | 374/20 |
| 4,216,669 | 8/1980 | Harding, Jr. | 374/20 |
| 4,276,768 | 7/1981 | Dadachanji | 374/28 |
| 4,376,583 | 3/1983 | Alford et al. | 356/237 |
| 4,629,333 | 12/1986 | Dosoretz et al. | 374/20 |
| 4,753,504 | 6/1988 | Kyogoku | 350/6.8 |
| 4,799,235 | 1/1989 | Bannell et al. | 374/18 |

FOREIGN PATENT DOCUMENTS 1836023 12/1960 Fed. Rep. of Germany.
58-44337 3/1983 Japan.
58-113839 6/1983 Japan.

OTHER PUBLICATIONS

Control and Instrumentation, (1983) vol. 15 No. 2.
Advances in Instrumentation 8131, vol. 37, (1982) Part 3, Research Triangle Park, NC. U.S.A.

Primary Examiner—William A. Cuchlinski, Jr.
Assistant Examiner—Diego F. F. Gutierrez
Attorney, Agent, or Firm—Browdy and Neimark

[57] ABSTRACT

An improved method of and an apparatus for measuring a very low water content in a non-condensible gas which has a dew point in the range of from ordinary temperature to −80° C. or less. The gas to be measured is pre-cooled to a temperature slightly higher than that of the dew point, and is then blown against a reflecting mirror whose surface is cooled down to the dew point temperature of the gas. A condensed light having high luminance is projected toward the reflecting mirror. When the gas is blown against the mirror and cooled down to the temperature of the dew point, thereof a dew or frost is formed on the mirror, and the amount of scattered light reflected from the mirror is increased by the dew or frost. This increase in scattered light is detected by a photodetector. A silicon wafer which is polished to have a surface precision of ¼ or less that of the wavelength of the condensed light is employed as the mirror to enable measurement of dew points of −80° C. or less.

14 Claims, 11 Drawing Sheets

Fig. 2'

Fig. 3 a. EXAMPLE 1
b. EXAMPLE 2

SECTION "A"

METHOD OF AND APPARATUS FOR MEASURING VERY LOW WATER CONTENT IN GAS

This application is a continuation-in-part application of U.S. Ser. No. 202,744 filed on June 6, 1988.

BACKGROUND OF THE INVENTION

1. Field of the Invention

The present invention relates to a method of and apparatus for measuring a very low water content in non-condensible gases which has a dew point of $-80°$ C. or less.

2. Description of the Related Art

As a result of the rapid developments in technology, utilization of inert gases, for example, $N_2$, Ar, $H_2$ and He, which have very low water contents, i.e., 0.5 ppm or less, (dew points of $-80°$ C. or less) has increased. In particular, material and carrier gases which are used for epitaxial growth and CVD in the semiconductor industry are required to have ultrahigh purities, and there is therefore a need to measure dew points of $-80°$ C. or less with a high degree of precision.

Many means for measuring the water content of a gas have heretofore been known. For example, as a means for measuring a dew point, one method has been known for a long time in which a change in the intensity of light which occurs when moisture contained in the gas to be measured has condensed on a cooled mirror surface is optically detected. As one type of optical detection method, absolute measurement is described in, for example, Industrial Instrumentation Handbook (Asakura Shoten, 1976), p. 297. According to this method, a variation in the intensity of the light reflected from a mirror surface is detected by the use of a freezing medium, a refrigerating machine and a thermoelectric cooler, and the temperature of the mirror surface at the time when any change in the light intensity is detected is measured to thereby obtain a humidity value which is basically taken from the dew point. The apparatus employed to practice this method has a cooled surface onto which light is projected from a light-emitting diode or a white light source, and the reflected light from the cooled mirror surface is received by a photodetector. In general, the mirror surface is cooled by a Peltier element, and as the surface is cooled, moisture contained in the gas to be measured becomes condensed or frozen on the cooled surface, so that the light projected on the adsorbed water molecules is partially absorbed or scattered, resulting in a decrease in the intensity of the reflected light. The change in the intensity of the reflected light is detected by the photodetector, and the temperature of the cooled mirror surface at the time when the intensity change occurs is measured to thereby measure the dew point of the gas concerned. There have been a rather large number of studies of dew-point instruments designed to measure the water content of a gas for industrial purposes with even more precision and on a continuous basis by using changes in the intensity of reflected light, e.g., Japanese Patent Publication (Kokai) Nos. 58-113840 (1983), 61-75235 (1986), U.S. Pat. No. 4,335,597, U.S. Pat. No. 4,345,455, etc.

Japanese Patent Publication (Kokai) No. 58-113839 (1983) also shows a method of measuring a dew point by detecting a change in the intensity of light scattered at an angle different from the reflection angle, rather than by measuring a change in the intensity of reflected light. More specifically, when moisture becomes condensed or frozen on a mirror surface, a sudden change occurs in the intensity of the light scattered by the condensate (or ice). Therefore, the temperature of the cooled mirror surface at the time when such an intensity change occurs is measured to thereby measure the dew point of the gas concerned. The principle of this method has been known for a long time and is described in Humidity and Moisture (Vol. 1), p. 165, Reinhold Publ. Co., New York, 1965. However, the measurable range of this method is shown to be between $-73°$ C. and $49°$ C., and it is therefore impossible with this prior art to realize measurement of low temperature dew points, as in the case of the present invention. In addition to the methods wherein the amount of water in a gas with a very low water content is measured by detecting an optical change that occurs when moisture contained in the gas becomes frozen on a cooled mirror surface, other methods have also been put into practical use wherein the amount of water in a gas with a very low water content is measured by detecting a change in the frequency of a crystal oscillator or a change in the electrostatic capacity which is caused by adsorption of water. However, none of these conventional methods is capable of measuring a dew point of $-80°$ C. or less with high accuracy.

The above-described method wherein the dew point of a gas is measured by detecting a decremental change in the intensity of the reflected light at the time when moisture contained in the gas has become condensed or frozen on a cooled mirror surface suffers from the problem that, as the water content in the gas becomes lower, that is, as the dew point becomes lower, the amount of condensate (or ice) decreases to an extreme degree, so that it is difficult to measure the dew point with a high degree of precision. Further, the prior art has the disadvantage that, when a gas flows slowly on a cooled mirror surface in the conventional arrangement, condensation (or freezing) of an extremely small amount of moisture takes place very slowly, and therefore no distinct change in the reflected light is shown, particularly when the dew point to be measured is $-80°$ C. or less. In the case of a very low water content, i.e., 10 [ppb] or less, water molecules are adsorbed on the mirror surface very gradually, so that it has heretofore been difficult to read any sudden change in the intensity of the reflected light. It is therefore effective to blow the gas to be measured against a cooled mirror surface from a nozzle-shaped (or pipe-shaped) member. However, with respect to a gas having a dew point of $-80°$ C., which has heretofore been considered capable of measurement with a substantially good degree of accuracy, it is necessary to precisely read the temperature of the cooled mirror surface at the time when the moisture contained in the gas in an extremely low amount, i.e., about 1 ppm, becomes frozen on the mirror surface; for a dew point of $-110°$ C., this amount is about 1/1000 of 1 ppm; and for a dew point of $-136°$ C., 1/1000 of 1/1000 of 1 ppm, that is, 1 ppt. There has accordingly been a demand for a technique of precisely measuring such a freezing point.

SUMMARY OF THE INVENTION

In view of the above-described problems of the prior art, it is a primary object of the present invention to provide a method of measuring a dew point of $-80°$ C. or less with a satisfactorily high degree of precision for the purpose of measuring the amount of water in a gas with a very low water content.

This invention relates to a method for measuring the amount of water in a gas with a very low water content which comprises using a dew-point meter or a frost-point meter comprising: a reflecting mirror of silicon wafer having a very smooth surface; a means for varying the temperature of the reflecting mirror from room temperature to around the boiling point of liquid nitrogen by a suitable cooling source; a gas ejecting nozzle disposed so as to face said reflecting mirror; means for projecting a condensed light ray onto that portion at which dew and/or frost is formed; and means for detecting a sudden increase in the intensity of scattered light, the process comprising:

a step of cooling a gas to be measured so that its temperature becomes close to that of the mirror without condensing or freezing the water content in said gas during said cooling;

a step of ejecting the gas from the said nozzle so as to hit said reflecting mirror;

a step of projecting a condensed light ray onto that portion of the reflecting mirror against which the gas to be measured is blown; and a step of detecting a sudden increase in the intensity of scattered light, thereby measuring a low dew point and/or frost point of −80° C. or less.

This invention also relates to an apparatus for measuring a dew point and/or a frost point comprising: a reflecting mirror whose temperature to be variable in the range of from room temperature to the temperature of liquid nitrogen, a reflecting surface of said reflecting mirror being very smooth; a gas ejecting nozzle disposed so as to face said reflecting mirror; means for projecting a condensed light ray onto that portion of the reflecting mirror against which a gas to be measured is ejected; and means for detecting a sudden increase in the intensity of scattered light.

Further, the present invention enables industrial measurement of the water content of gases, for example, nitrogen, argon, hydrogen, helium, etc., which have dew (frosting) points of −80° C. or less, by precisely measuring the condensation (freezing) temperature with a combination of a cooling means such as a helium refrigerating machine and a heater, although it is intermittent measurement based on rises and falls in temperature. Japanese Patent Publication (Kokai) No. 58-44337 (1983) has already disclosed a method of precisely measuring a dew point with a reduced likelihood of error by means of an apparatus which is provided with a pre-cooling section for previously cooling a gas to be measured before it is blown against a cooled reflecting mirror and a nozzle for blowing the gas cooled in the pre-cooling section against the reflecting mirror. It is also a critical factor in precise measurement of a dew point to maintain the temperature inside the measuring chamber as close to the temperature of the cooling section as possible during any measurement carried out at low temperatures.

In a method wherein a gas to be measured flows slowly on a cooled reflecting mirror, if the dew (frosting) point which is to be measured is very low, i.e., −80° C. or less, it is not easy to cool the gas down to the temperature of the cooled reflecting mirror unless the gas is previously cooled down to a temperature as close to the dew (frosting) point of the gas as possible. If no pre-cooling is carried out, the temperature of the cooled reflecting mirror which is measured when moisture contained in the gas becomes condensed or frozen on the reflecting mirror may be considerably lower than the actual dew (frosting) point of the gas, which results in a large error. Accordingly, in order to read accurately the temperature at which an extremely small amount of moisture contained in a gas starts to freeze, it is necessary to previously cool the gas down to a temperature close to the dew (frosting) point thereof but without condensing or freezing the water content, blow the gas against the reflecting mirror from a nozzle-shaped member, and irradiate a limited portion of the reflecting mirror with a light ray condensed as much as possible. In this way, a sudden increase in the intensity of the scattered light which is generated when the light ray is reflected from the reflecting mirror is measured to thereby enable measurement of the dew (frosting) point of a gas having a very low water content.

Since the gases blown against the mirror contain fine ice leaves which are cooled down to −80° C. or less and have a high degree of hardness the reflecting mirror is required to have a high degree of hardness. Further, the reflecting mirror must be smooth and must have high reflectance and high thermal conductivity.

The ejecting angle of the gas to be measured onto the mirror may be in the range of 30° C.–60° C. with respect to the reflecting mirror.

The above and other objects, features and advantages of the present invention will become apparent from the following description taken in conjunction with the accompanying drawings.

DESCRIPTION OF THE PREFERRED EMBODIMENTS

Embodiments of the present invention will be described hereinunder in detail with reference to the drawings attached thereto. It should be noted that the present invention is not necessarily limited to the arrangement shown in these drawings.

Figure 1:
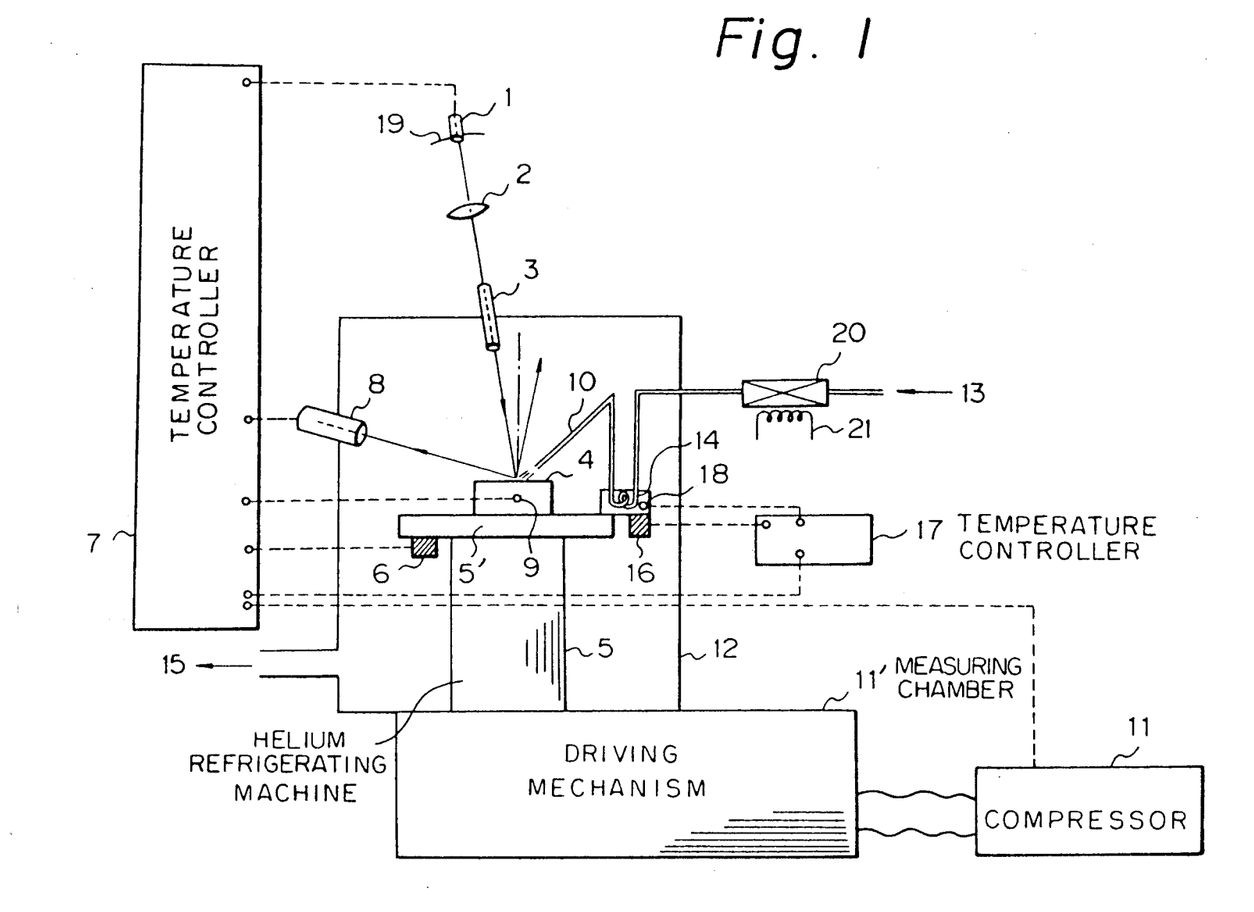
FIGS. 1, 2 and 2' are schematic views respectively showing apparatuses employed to practice the method according to the present invention.

FIG. 1 shows one embodiment of the present invention.

Light which is emitted from a light source 1 is converged in the form of parallel rays by a parabolic mirror 19 and then applied to a reflecting mirror 4 through an entrance window 3 after passing through a condenser lens 2 so that the parallel rays are condensed on the reflecting mirror 4 as much as possible. The incident light is reflected by the reflecting mirror 4, and the light which is scattered at the reflecting mirror 4 is measured by a photodetector 8. The photodetector 8 is installed on an optical path having an angle which is different from the reflecting light. The reflecting mirror 4 is fixed on the cold surface 5' of a helium refrigerating machine 5 so that the reflecting mirror is in contact with the cold surface 5' to a thermally adequate degree. The cold surface 5' is formed of a good thermal conductor such as copper. The helium refrigerator 5 is connected with a driving mechanism 11' which drives the helium refrigerating machine 5 and a compressor 11 which compresses the helium gas. Consequently cooling is made to occur on the cold surface 5' of the helium refrigerator 5. The arrangement is such that the temperature of the reflecting mirror 4 is capable of being raised or lowered as desired by a combination of a heater 6, a thermocouple 9 and a temperature controller 7.

A gas to be measured is introduced as shown by the reference numeral 13 through a filter 20. The filter 20 is formed of a hydrophobic material and heated up to 200° C. by a heater 21 such that removal of any particulate foreign matter alone can be effected. A heater 16 and a precooler 14 are provided between the nozzle 10 and the filter 20 so that the gas to be measured is pre-cooled to a temperature slightly higher than that of the reflecting mirror 4 so that condensation of the water content in the precooler 14 is prevented. Although it is preferable that the temperature of the gas ejected from the nozzle 10 is close to that of the reflecting mirror 4 for the sake of the accuracy of the dew point measurement, it is not desirable for it to be too close because the water content of the gas will then condense in the precooler 14 to cause inaccurate measurement. The gas to be measured generally can be pre-cooled to an appropriate temperature slightly higher than that of the dew point depending on an optimized design for the surface area of the precooler 14 and the flow rate of the gas to be measured. Otherwise, as shown in FIG. 1, the temperature of the pre-cooler 14 should be controlled by a thermocouple 18 and a temperature controller 17. After being blown against the reflecting mirror 4, the gas to be measured is discharged from the system as shown by the reference numeral 15.

When the gas blown against the reflecting mirror 4 is cooled so as to form an infinitesimal frosting on the reflecting mirror 4 the amount of scattered light suddenly increases and this is detected by the photodetector 8. In this way, the dew point of the gas can be detected.

The reflecting mirror 4 is preferably made of a material having a thermal conductivity which is as high as possible, for example, copper, brass, aluminum or silicon crystal. The reflecting surface of the reflecting mirror 4 should be ground as smooth as possible and the surface precision is preferably determined so as to correspond to ¼ or less of the wavelength λ of the light source. These are requirements which must be met in order to minimize the light scattered at the reflecting mirror 4 and to allow precise detection of any increase in the intensity of scattered light caused by freezing of a very small amount of moisture at the freezing point. Further, it is important that the incident light is focused on the reflecting mirror 4 as precisely as possible. The present inventors have found experimentally that employment of a ray of light which is itself condensed, such as a beam emitted from helium-neon laser or laser diode, is, of course, one of the means that can be used for effectively improving the sensitivity.

In addition, increasing the reflectivity of the reflecting mirror 4 by deposition of gold or aluminum is, of course, one of the effective means for increasing the sensitivity. It is also a matter of course that improving the surface hardness of the reflecting mirror 4 by coating it with a thin film of titanium nitride, aluminum nitride, silicon oxide, aluminum oxide or the like is one of the effective means for maintaining the smooth surface condition of the reflecting mirror 4 for a long period of time. Since silicon wafer is a good helium-neon laser light absorbing material, its surface is not a good reflecting surface.

Figure 4:
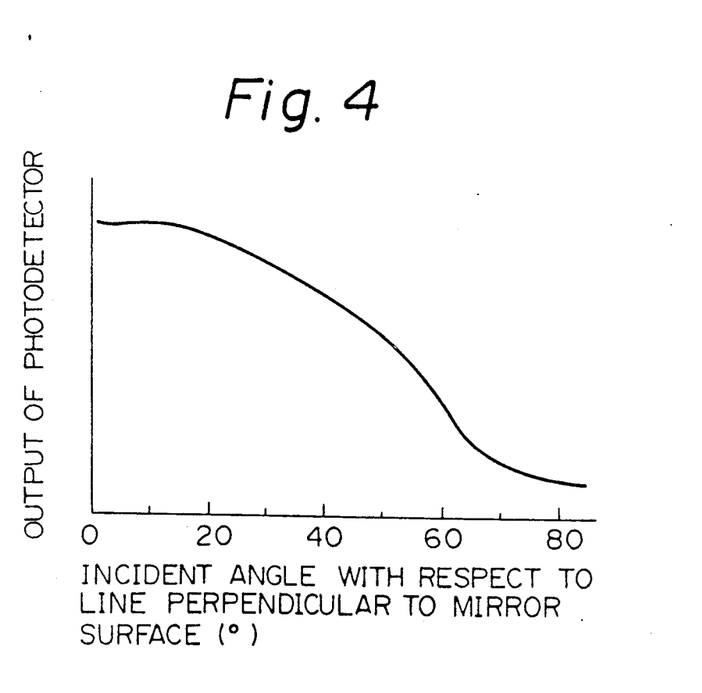
FIG. 4 is a graph showing the relationship between the incident angle with respect to a line perpendicular to the reflecting mirror and the output of the photodetector.

However, the surface smoothness of silicon wafer is considerably high; according to the experiment carried out by the present inventors, it is possible to measure a dew point near −120° C. From this point of view, a high reflectance is not an absolutely necessary condition. Accordingly, it is preferable for a precise measurement of the dew point to employ a material as the reflecting mirror, which has a smooth surface, low amount of light scattering, a good thermal conductivity, a hardness and a high reflectance. The hardness is required to be enough to maintain the surface condition constant for a long period of time under a blow from the nozzle by fine and hard particles of alumina or silica which are contained in the gas, oxide particles of Fe, Ni, Cr, Cu, etc. which are generated from piping materials and fine ice crystal. In particular, it is most preferable to employ a reflecting mirror made of a silicon wafer which is formed of a 111 or 100 cleavage surface of silicon crystal, thoroughly polished, coated with aluminum thin film by vacuum deposition or sputtering, and further coated with an aluminum nitride thin film of 1000 Å or less as a protective film. It is considered that the aluminum nitride thin film is an ideal protective film for the reflecting mirror, since it has good thermal conductivity, high hardness and high transparency. In addition, in order to effectively measure a very low water content in even a gas having a dew point of −80° C. or less on the basis of the frosting point, it is absolutely necessary to apply condensed light to that position on the reflecting mirror 4 where the gas to be measured is blown from the nozzle 10. The present inventors measured the incident angle of light under various conditions and as a result, have found that, as the incident angle becomes closer to 0° with respect to a line perpendicular to the reflecting mirror 4, the degree of sensitivity with which a sudden change in the intensity of scattered light can be read becomes higher. When a light-emitting diode is employed as the incident light source 1, the sensitivity becomes higher as the incident angle becomes closer to 0° with respect to the line perpendicular to the reflecting mirror 4, as shown in FIG. 4. The results of the measurement show that, as the incident angle becomes closer to 0° with respect to the perpendicular, more condensed light is applied to the reflecting mirror 4. It has been shown that the incident angle is preferably set at 60° or less, particularly preferably, 10° or less.

In order to enable measurement of a very low water content, it is essential to heat the sampling piping by means of a heater. With a view to precisely measuring a very low water content by the dew (frosting) point method, it is particularly important to heat the gas to a temperature near 200° C. together with a filter which is capable of removing foreign particles flowing together with the gas and thereby constantly maintain the sampling piping and the like within the system in a condition wherein the amount of adsorbed water is reduced.

All the above-described constituent elements are cooled down to low temperature. The measuring chamber therefore needs appropriate thermally insulating means (including a vacuum).

In such a case, since the temperature inside the chamber 12 changes, the luminance of the light-emitting diode 1 changes, and this may hinder precise measurement of the scattered light by means of the photodetector 8.

Figure 2:
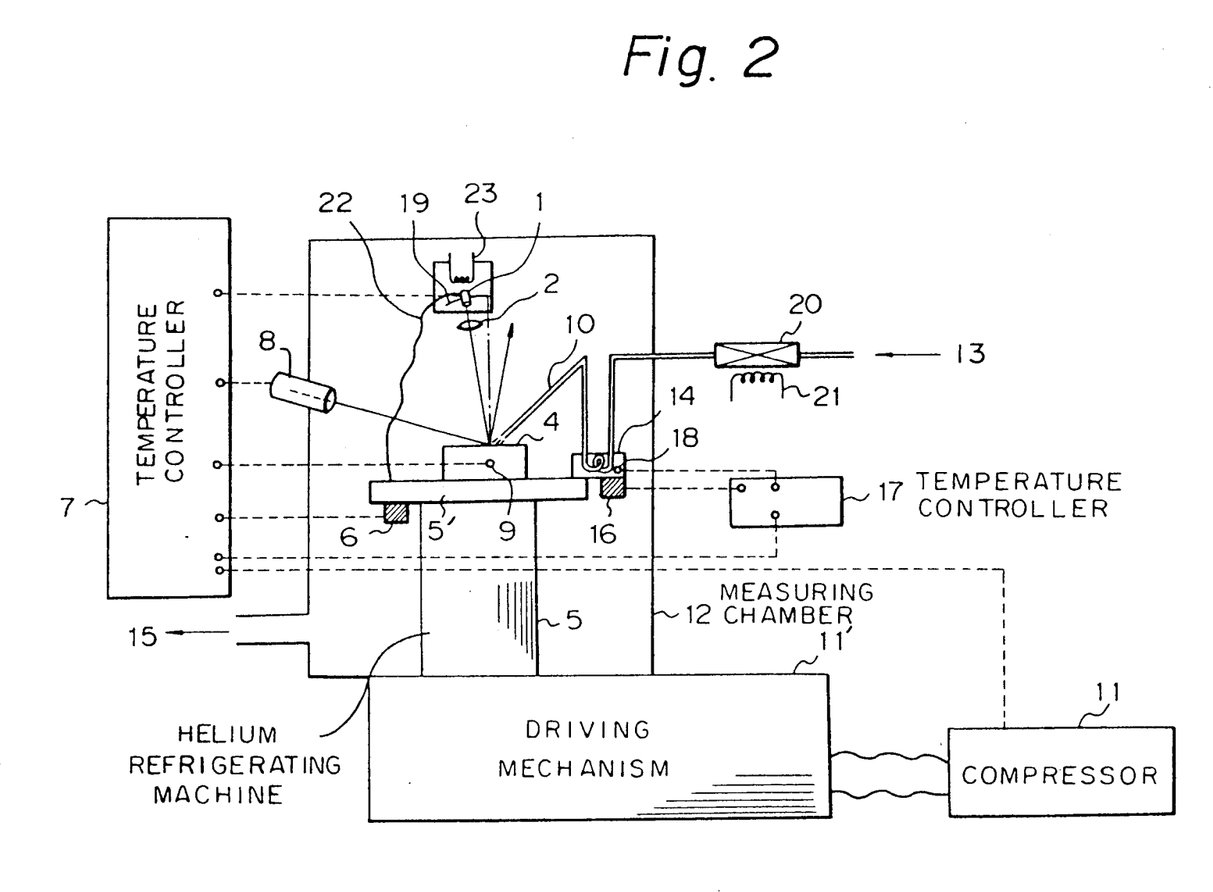

FIG. 2 shows another embodiment according to the present invention in which the light-emitting diode 1, the parabolic mirror 19 and the condenser lens 2 are disposed in a measuring chamber 12. The cold surface 5' of the helium refrigerating machine 5 and the light-emitting diode 1 are brought into thermal contact with each other by the use of an appropriate copper wire or rod 22, and the temperature of the light-emitting diode 1 is maintained at a constant temperature, i.e., between $-20°$ C. and $-30°$ C., by temperature control effected by means of a heater 23, thereby preventing any change in the luminance of the light-emitting diode 1 due to temperature changes.

FIG. 2' shows an embodiment of the present invention in which the reflecting mirror 4 is cooled by a low temperature liquefied gas such as liquid nitrogen instead of the helium refrigerator system 5, 11, 11', and the light-emitting diode 1 and the photodetector 8 are respectively cooled by the thermoelectric refrigerator 30 and 30' so as to broaden the dew point measuring range to a much lower temperature.

The helium refrigerator per se is well known, is expensive and involves problems in that noises and vibrations due to the compressor, piston, spacer and so on are caused, and in that special maintenance is required. There are some cases such as a semiconductor factory in which it is more easy and more economical to cool with liquid nitrogen, since a large quantity of liquid nitrogen is generally used as a purge gas in such places. In FIG. 2', the liquid nitrogen in a liquefied gas container 24 is blown against a cold surface 5' having good thermal conductivity such as copper from a tube 11 after flow control has been effected by means of a stop valve 25 and a needle valve 26. In this way, the reflecting mirror 4 is rapidly cooled. Evaporated gases are discharged from an outlet 28.

The light-emitting diode 1 is cooled by a thermoelectric refrigerator 30 so as to reduce the level of noise. Then the light in which noise has been reduced is condensed and irradiated on the reflecting mirror 4.

In addition, the photodetector 8 is cooled by the thermoelectric refrigerator 30' so that the level of noise therein is lowered.

When an infinitesimal frosting occurs on the reflecting mirror 4, the amount of scattering light suddenly increases, and this is detected by the photodetector 8. Immediately thereafter, the valve 27 which is disposed on the liquefied gas supply line is closed, and the cold surface 5' is heated by the heater 6 so as to break the frost. The other operations of this apparatus are the same as that of the apparatus of FIG. 1.

Figure 13:
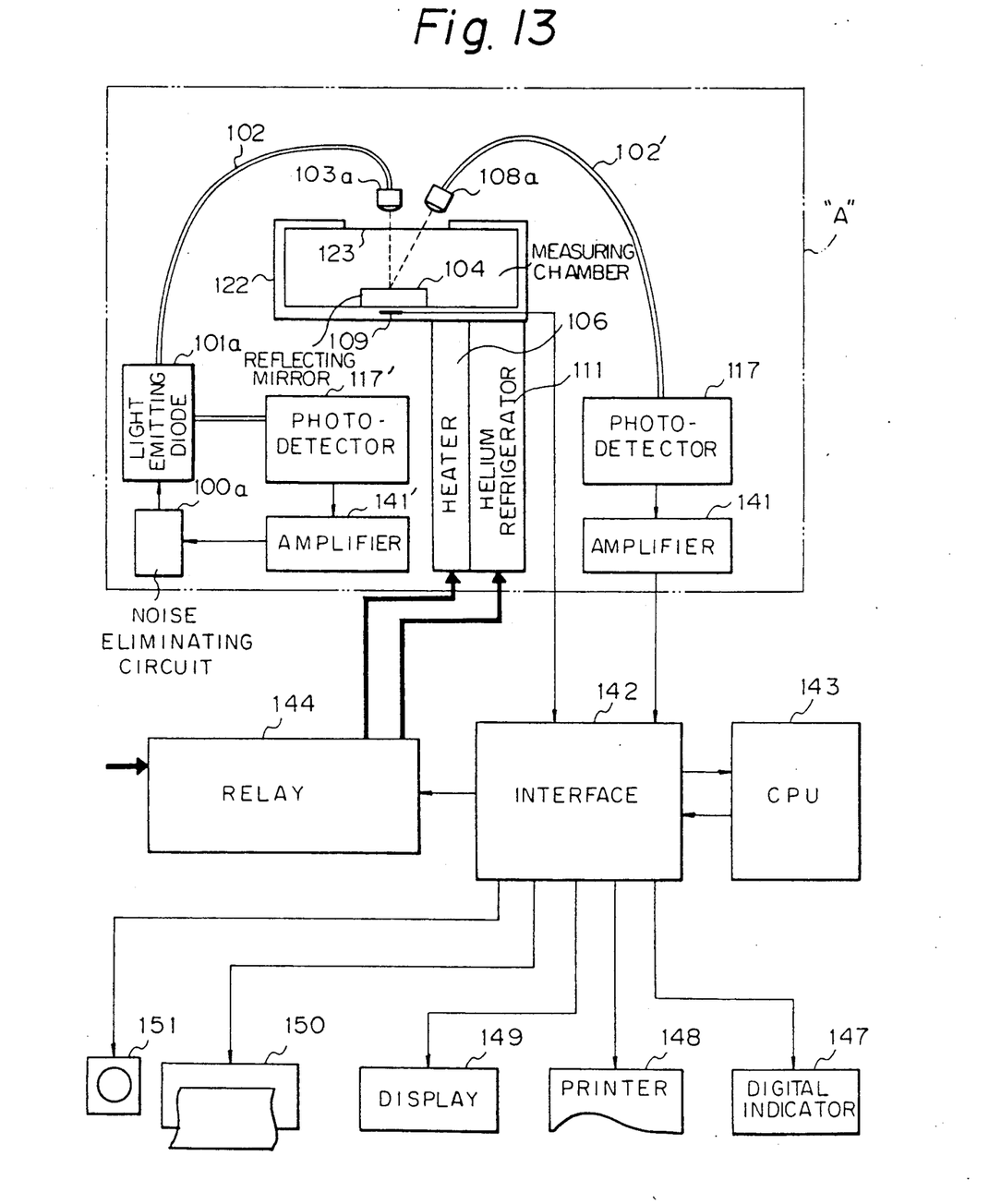
FIGS. 13 and 14 are schematic views respectively showing processes for detecting the dew point using a computer.

FIG. 13 shows an embodiment of the present invention in which measurement of the dew point is processed using a CPU (central processing unit). A measuring chamber 122 and a reflecting mirror 104 are cooled by a helium refrigerator machine 111. In this apparatus, a light from a light-emitting diode 101a is transmitted to a condenser lens 103a through an optical fiber 102, condensed by the condenser lens 103a and then irradiated on the reflecting mirror 104. The light irradiated on the reflecting mirror 104 is scattered on the reflecting mirror 104 and detected by a photodetector 117 through a condenser lens 108a and an optical fiber 102'.

When a gas to be measured is blown onto the reflecting mirror 104 from a nozzle (not shown) and an infinitesimal amount of water in the gas is frosted on the reflecting mirror 104, the amount of scattered light increases. The increased amount of scattered light is condensed by the condenser lens 108a and detected by the photodetector 117 through the optical fiber 102'. Since the output level of the photodetector 117 is very low, particularly in a case in which the dew point is relatively low, the output of the photodetector 117 is supplied to an amplifier 141 for amplification. An output of the amplifier 141 is supplied to CPU 143 through an interface 142. When there are noises in the light-emitting diode 101a, the noises are also amplified by the amplifier 141, this resulting in a misreading of the signal. Thus, a feedback circuit comprising a photodetector 117', an amplifier 141' and a noise eliminating circuit 100a is provided in order to eliminate the noises. That is, a portion of the light from the light-emitting diode 101a is supplied to a photodetector 117' which is the same as the photodetector 117. An output of the photodetector 117' is then supplied to the amplifier 141' to be amplified. The amplified output is supplied to the noise eliminating circuit 100a, and the noise eliminating circuit 100a feeds back an output corresponding to the noise to an input of the light-emitting diode 101a so as to eliminate the noise from the light-emitting diode 101a. The result is that only the output caused by the scattered light is supplied so that the detectable limit of the dew point measurement range is lowered. The temperature of the reflecting mirror 104 is measured by a temperature sensor 109, and the output of the temperature sensor 109 is supplied to CPU 143 through the interface 142. CPU 143 recognizes dew point and determines dew point temperature, with receiving the reflecting mirror temperature signal from the temperature sensor 109 and the suddenly increasing output from the photodetector 117 and supplies respective suitable output signals to a digital indicator 147, a printer 148, a display 149, and an analogue recorder 150 and an alarm 151, through the interface 142. A relay 144 controls each of the power supplies of a helium refrigerator 111 and a heater 106. For example, when the dew point measurement is completed, the helium refrigerator 111 is stopped in response to a signal from the relay 144, and the heater 106 starts in response to a signal from the relay 144 so as to break the frost on the reflecting mirror 104.

Figure 14:
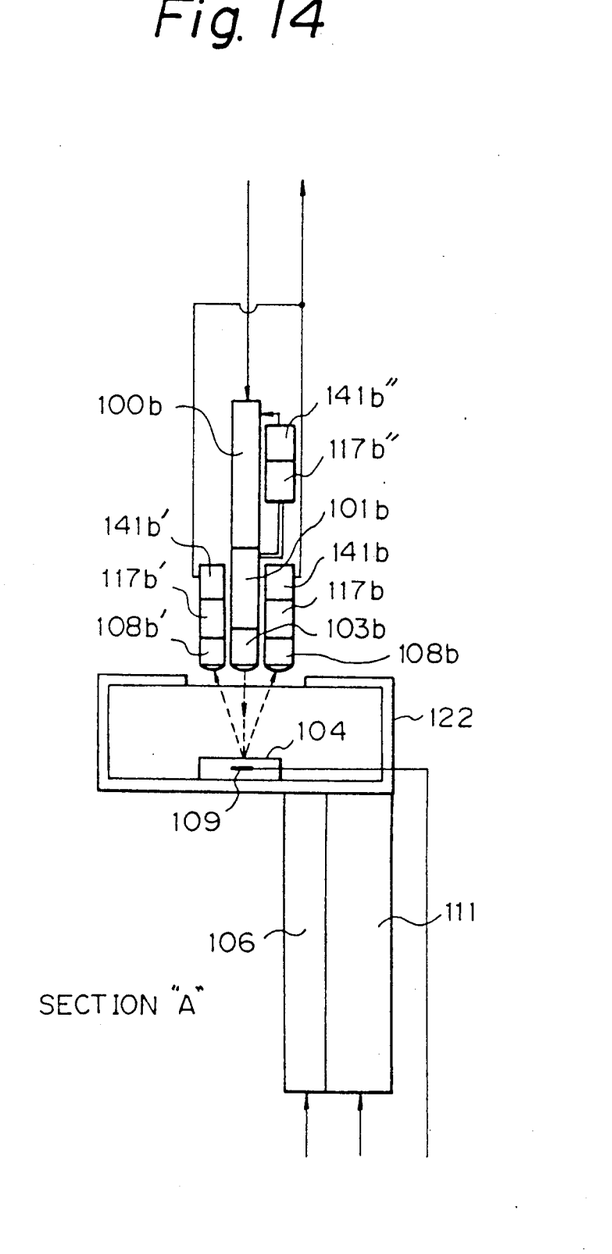

FIG. 14 shows an embodiment of a portion "A" in FIG. 13. A light-emitting diode 101b and a condenser lens 103b are coaxially disposed on the center axis of the reflecting mirror 104. The output of the light-emitting diode 101b is controlled by a feedback circuit which comprises a photodetector 117b'', an amplifier 141b'' and a noise eliminating circuit 100b. The scattered light from the reflecting mirror 104 is condensed by condenser lenses 108b, 108b', detected by photodetectors 117b, 117b' and amplified by amplifiers 141b, 141b', respectively. The other operations are the same as those of FIG. 13. Although two condenser lenses 108b, 108b' are used in this embodiment, more than two condenser lenses may be used so as to further increase the measuring sensitivity.

The present invention will be explained more specifically below by way of Examples. However, the present invention is in no way restricted to these Examples.

EXAMPLE 1

With the arrangement shown in FIG. 1, a gas generated from liquid nitrogen by evaporation was supplied as the gas to be measured to the reflecting mirror 4 from the nozzle 10, light from the light-emitting diode 1 that had been condensed as much as possible by the parabolic mirror 19 and the condenser lens 2 then being projected on the reflecting mirror 4, and the light scattered at the reflecting mirror 4 received by the photodetector 8. As the reflecting mirror 4 was gradually cooled by means of the small-sized helium refrigerating machine 5, moisture contained in the gas to be measured became frozen on the reflecting mirror 4, resulting in an increase in the intensity of the scattered light received by the photodetector 8. The temperature of the reflecting mirror 4 at this time was measured by means of the thermocouple 9. The temperature was $-118°$ C., and thus the dew point of this gas was found to be $-118°$ C. Thus, it was possible to measure a dew point so low that it had heretofore been impossible to measure. The relationship between the temperature of the reflecting mirror 4 and the output of the photodetector 8 is shown by the line a in FIG. 3. It should be noted that a silicon wafer employed in the semiconductor industry was employed in this Example as the reflecting mirror, and the light from the light-emitting diode that was condensed as much as possible was made incident on the reflecting mirror at $5°$ with respect to the perpendicular.

EXAMPLE 2

An experiment was conducted with the same arrangement as in Example 1 except that the light-emitting diode 1, the parabolic mirror 19 and the condenser lens 2 were installed inside the measuring chamber 12 so as to maintain the light-emitting diode 1 at the constant temperature of $-20°$ C. as shown in FIG. 2.

Figure 3:
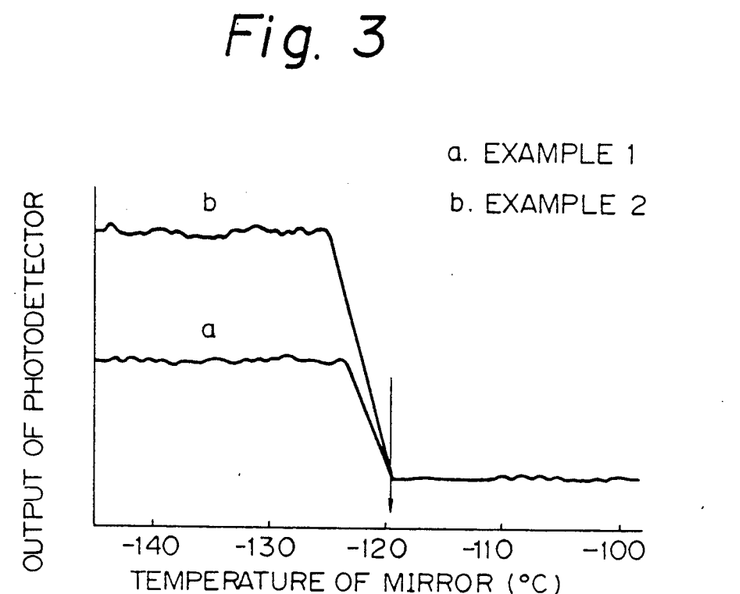
FIG. 3 is a graph showing the relationship between the temperature of the reflecting mirror and the output of the photodetector.

With this arrangement, an experiment similar to that in Example 1 was carried out. As a result, it was possible to conduct measurement with a higher sensitivity than that in the case of Example 1. The line b in FIG. 3 shows the relationship between the temperature of the reflecting mirror 4 and the output of the photodetector 8. Thus, it was confirmed that the arrangement shown in FIG. 2 also enables precise measurement of a low dew point, i.e., $-80°$ C. or less.

EXAMPLE 3

Figure 11:
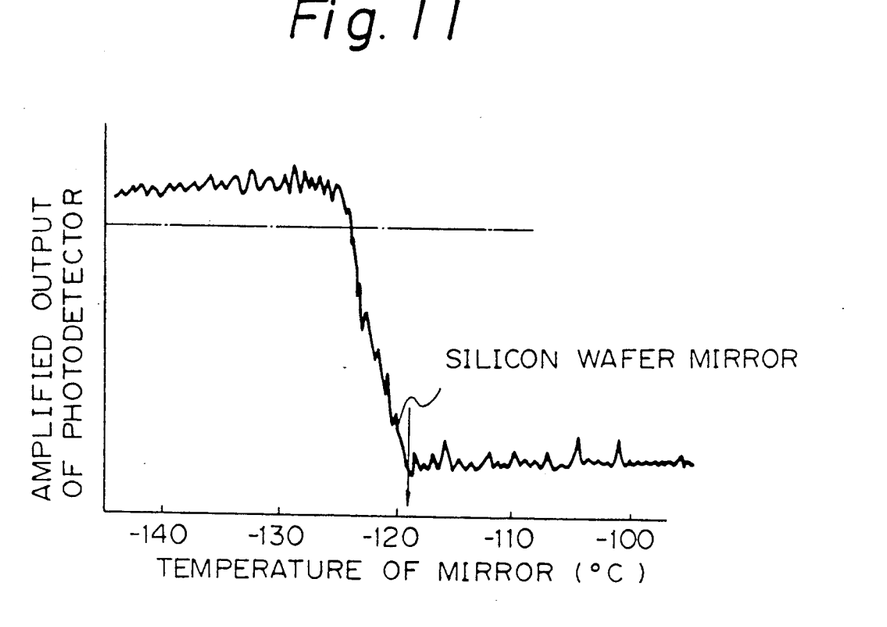
FIGS. 11 and 12 are graphs respectively showing the relationship between the temperature of the reflecting mirror and the amplified output of the photodetector.

It is very difficult to automatically and accurately execute a dew point measurement such as that of Example 1 using CPU. As the output level of the photodetector is low at $-118°$ C., it is very difficult to distinguish the signal due to the dew point from noise even when most of the noises have been previously eliminated. The level of the signal due to the dew point needs to be from several times to about ten times the remaining noise level. The scattered light was measured by the system shown in FIGS. 13 and 14 employing a silicon wafer as the reflecting mirror. FIG. 11 shows an amplified signal of the output of the photodetector in this case. The level shown by a chain line represents the measuring limit which can be detected using CPU. By employing the silicon wafer as the reflecting mirror, the signal level due to the dew point was increased so as to be accurately distinguished from noise.

EXAMPLE 4

Figure 12:
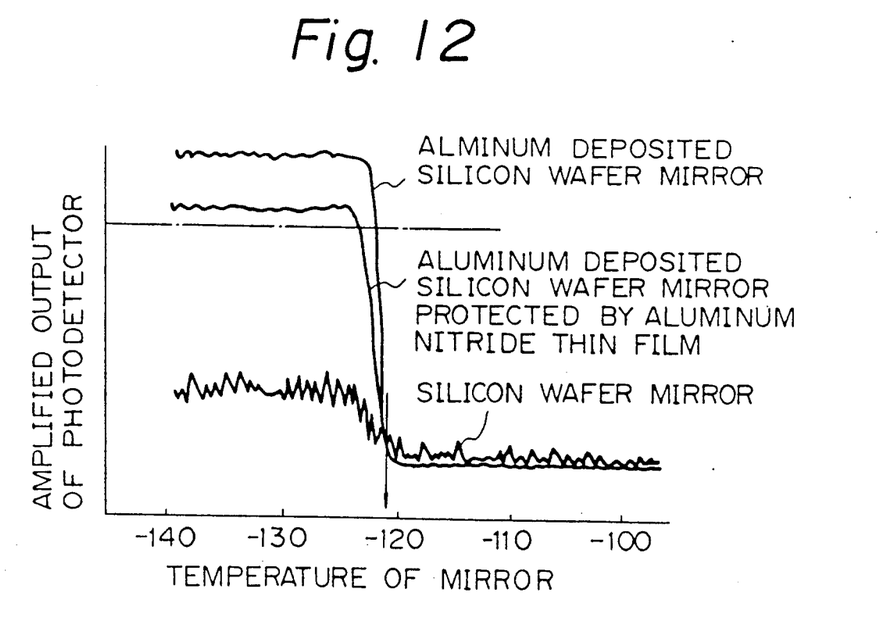

In the method of Example 3, a silicon wafer coated with an aluminum thin film and an aluminum nitride thin film each having a thickness of 1000 Å was employed as the reflecting mirror for measuring the dew point at $-120°$ C. or less. The result of measurement is shown in FIG. 12. By using this type of reflecting mirror, the S/N ratio was raised so as to accurately specify the dew point at $-122°$ C. However, as also shown in FIG. 12, the dew point could not be specified by the CPU at $-122°$ C. in the case of using the silicon wafer, since the silicon wafer has high absorptivity and low reflectance, and the S/N ratio is too low. A silicon wafer coated with only the aluminum thin film has high reflectance and results in a high S/N ratio level.

However, the reflectance of the aluminum thin film coated silicon wafer was gradually reduced to 60% over a period of 2 to 3 hours, and the aluminum thin film was peeled off after 100 hours. When an aluminum nitride thin film was further coated on the aluminum thin film the reflectance of the reflecting mirror was reduced to 90 to 95%. However, the reflectance did not vary for a long period of time, since the aluminum thin film was completely protected by the transparent aluminum nitride thin film.

COMPARATIVE EXAMPLE 1

Figure 5:
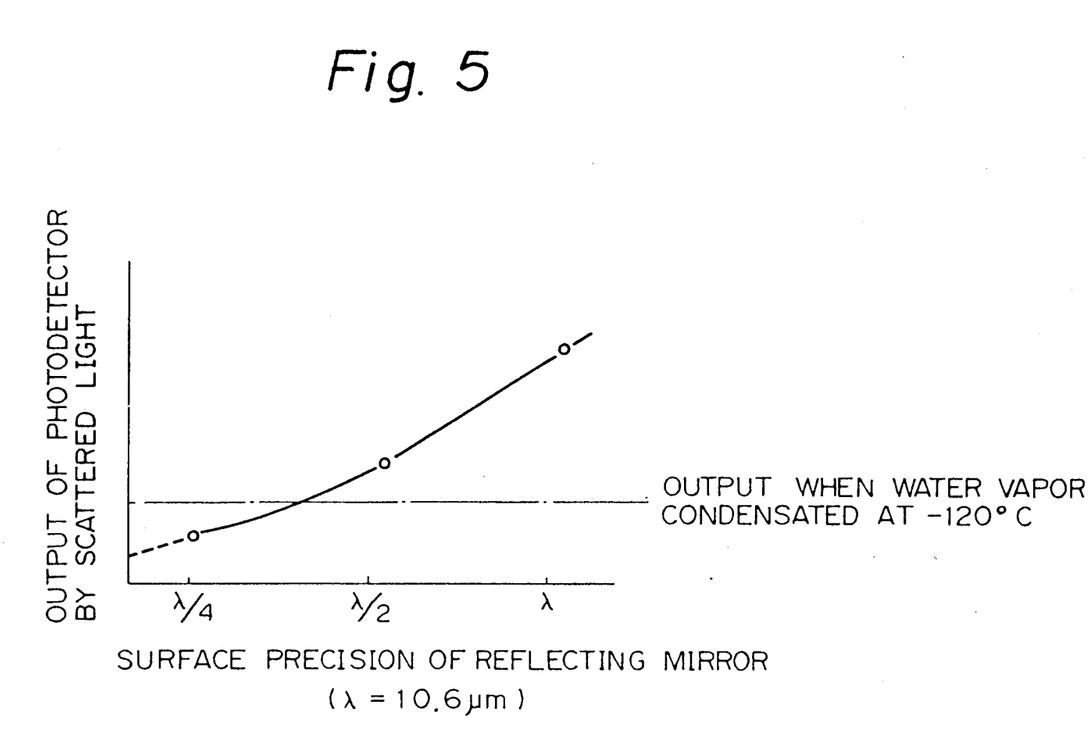
FIG. 5 is a graph showing the relationship between the surface precision of the reflecting mirror and the output of the photodetector by the scattered light on the reflecting mirror.

With the arrangement of Example 1, a copper surface was ground so that the surface precision corresponded to the measuring wavelength $\lambda$ ($\lambda = 10.6$ $\mu$m), and light from the light-emitting diode 1 that was condensed as much as possible was projected on the reflecting mirror 4 in the same way as in Example 1. As a result, even when the moisture contained in a gas to be measured had not yet frozen, the intensity of the scattered light was higher than that measured when the moisture became frozen in Example 1. Further, even when the moisture became frozen, there was not change in the output of the photodetector 8. Similar experiments were conducted with the surface precision of the copper surface serving as a cooled reflecting mirror changed to varying degrees. The results, showed that it is impossible to measure the dew point (e.g., $-120°$ C.) of a gas containing an extremely small amount of moisture when the surface precision corresponds to $\frac{1}{4}$ or more of the measuring wavelength $\lambda$ ($\lambda = 10.6$ $\mu$m). FIG. 5 shows changes in the output of the photodetector 8 occurring when the surface precision was changed from $\lambda$ ($\lambda = 10.6$ $\mu$m) to $\lambda/4$.

COMPARATIVE EXAMPLE 2

Experiments similar to Example 1 were conducted with the same arrangement as in Example 1 except that the parabolic mirror 19 and the condenser lens 2 were removed from the arrangement shown in FIG. 1.

Figure 6:
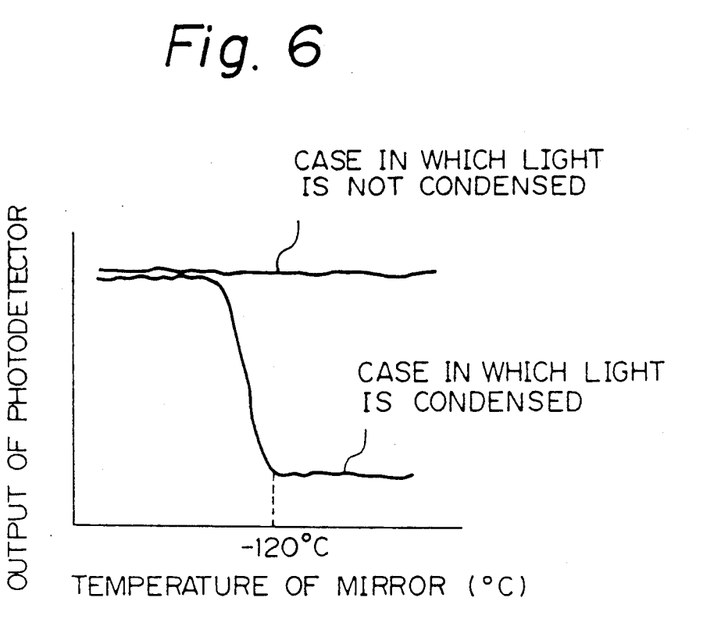
FIGS. 6 to 9 are graphs showing the relationship between the temperature of the reflecting mirror and the output of the photodetector under various conditions.
Figure 7:
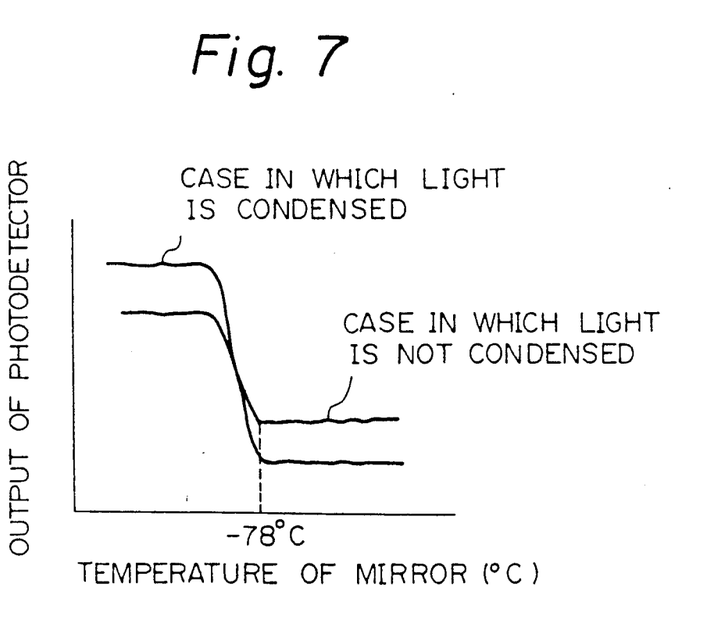

When the light from the light-emitting diode 1 was not focused on the reflecting mirror 4, it was possible to measure a dew point as low as −78° C., but it was impossible to detect an increase in the intensity of the scattered light in the case of moisture-containing gases having respective dew points lower than −78° C. FIGS. 6 and 7 show results obtained in the case where the dew points of the gases tested were −120° C. and −78° C., respectively. As will be understood from these figures, in order to measure a low dew point, i.e., −80° C. or less, the light which is projected on the reflecting mirror 4 must be condensed as much as possible.

COMPARATIVE EXAMPLE 3

Figure 8:
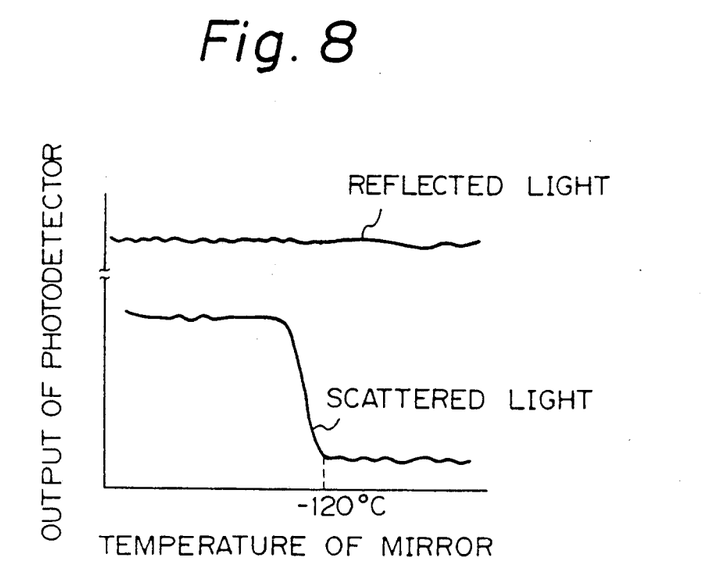
Figure 9:
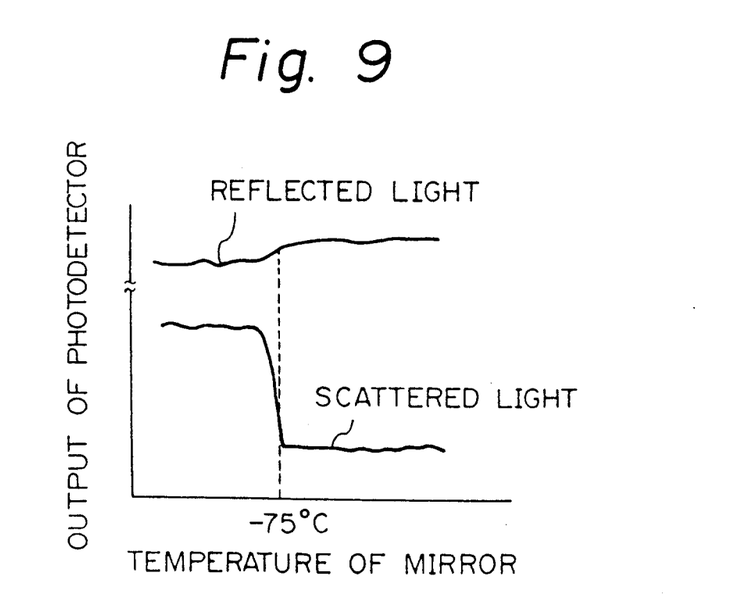

Experiments similar to Example 1 were conducted with the same arrangement as in Example 1 except that the photodetector 8 was installed in the optical path of the reflected ray. Helium-neon laser light and light from a light-emitting diode that was condensed as much as possible were employed as the light projected on the reflecting mirror 4. In this case, the decrease in the intensity of the reflected light was very small irrespective of the type of light source. The results of these experiments are shown in FIGS. 8 and 9. It will be understood from these results that, in the case where a dew (frosting) point is measured by detecting a decrease in the intensity of the reflected light, it is impossible to measure a dew (frosting) point of −75° C. or less.

COMPARATIVE EXAMPLE 4

One method which does not employ the technique of measuring the amount of moisture contained in a gas by causing the gas to become attached to a reflecting mirror by condensation or freezing to allow optical detection of the attached condensate or ice is the method wherein the water content of a gas is measured on the basis of changes in the electrostatic capacity of a sensor comprising a thin film of aluminum oxide which is coated with gold by deposition. This known method is shown in JIS-K0226 as a method of measuring a water content of 2 (ppm) or more. With this method, nitrogen gases having respective dew points of from 0° C. to −90° C. were measured. The results showed that no change was to be seen in the electrostatic capacity in the case of nitrogen gases having dew points of −80° C. or less.

Figure 10:
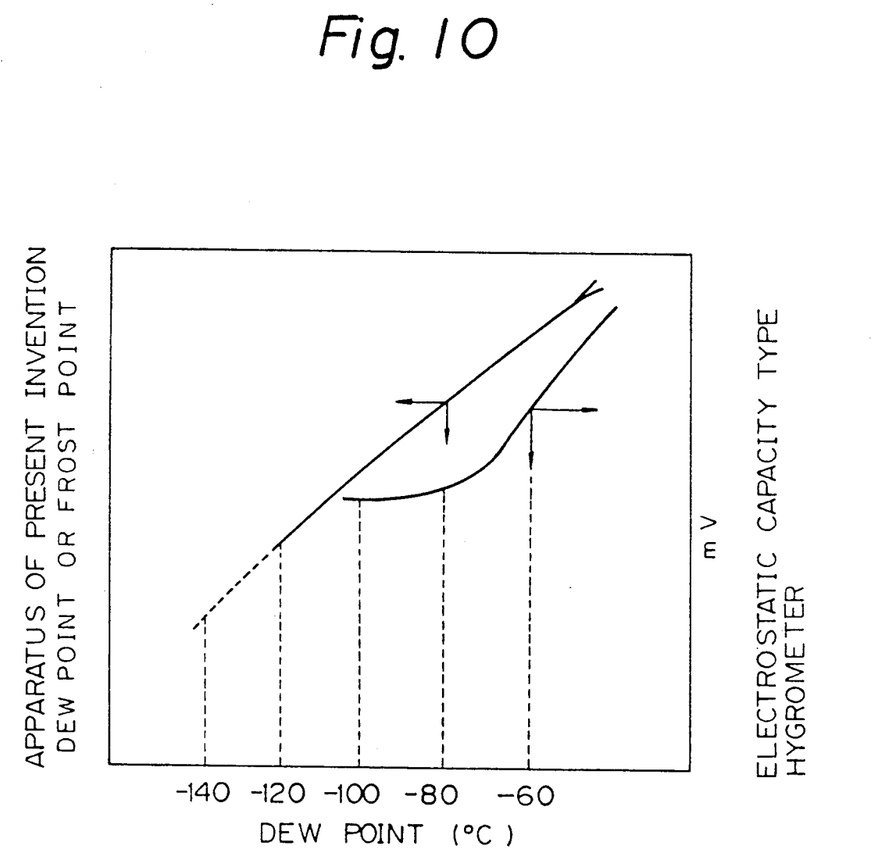
FIG. 10 is a graph showing the relationship between the output of a conventional electrostatic condenser type hygrometer and the output of the photodetector of the water content measuring apparatus according to the present invention.

FIG. 10 shows a comparison between the output of the electrostatic condenser type hygrometer and the output of the water content measuring apparatus according to the present invention.

As has been described in detail, the apparatus according to the present invention is provided with a pre-cooling section for previously cooling a gas to be measured before it is blown against a reflecting mirror and nozzle for blowing the pre-cooled gas against the reflecting mirror. Further, a light ray which is condensed as much as possible is used as a light source to be projected onto the reflecting mirror, silicon wafer having a surface precision of ¼ or less of a wavelength of a light is used as a reflecting mirror, and the condition of moisture as condensed or frozen on the reflecting mirror is detected by the light scattered at the reflecting mirror. Thus, it is possible to measure electrically and precisely the water content of a gas having a dew point in the range of from ordinary temperature to −80° C. or less.

What is claimed is:

1. A method for measuring the amount of water in a gas with a very low water content at a temperature of −80° C. or less by using a dew point meter or a frost-point meter comprising: a reflecting mirror having a temperature that is variable in a range of from room temperature to the temperature of liquid nitrogen, λ wherein a reflecting surface of said mirror is formed of a silicon wafer having a surface precision of ¼ or less of the wavelength λ of a light source radiated thereon; means for cooling said reflecting mirror to a predetermined temperature; a gas ejecting means for ejecting toward said reflecting mirror a gas to be measured; means for projecting a condensed light ray onto a portion of said reflecting mirror at which said gas is blown; and means for detecting any sudden increase in the intensity of scattered light which is caused by said dew and/or frost, said method comprising:

cooling a gas to be measured so that its temperature becomes close to that of the mirror without condensing or freezing the water content of said gas during said cooling;

ejecting the gas from said nozzle so as to hit said reflecting mirror;

projecting a condensed light ray onto that portion of the reflecting mirror against which the gas to be measured is ejected;

detecting any sudden increase in the intensity of scattered light on said reflecting mirror and measuring the predetermined temperature of said reflecting mirror with a thermocouple at said sudden increase in the intensity of scattered light, wherein said predetermined temperature corresponds to the dew point or frost point of the gas, and said dew point or frost point is used to obtain a humidity value which corresponds to the amount of water in the gas.

2. The method of claim 1, wherein said step of cooling a gas to be measured is executed by using a low-temperature liquefied gas.

3. The method of claim 1, wherein said step of cooling a gas to be measured is executed by using liquid nitrogen.

4. The method of claim 1, wherein said condensed light ray is projected toward the reflecting mirror at an incident angle of 60° with respect to a line perpendicular to said reflecting mirror.

5. The method of claim 1, wherein said reflecting surface of said mirror is coated with an aluminum thin film.

6. The method of claim 5, wherein said reflecting surface is further coated with a protective film having good thermal conductivity, high hardness and high transparency.

7. The method of claim 6, wherein said protective film is an aluminum nitride thin film.

8. An apparatus for measuring the amount of water in a gas with a very low water content at a temperature of −80° C. or less by measuring a dew point or frost point comprising:

a reflecting mirror having a temperature that is variable in a range of from room temperature to the temperature of liquid nitrogen and having a reflecting surface formed of a silicon wafer having a surface precision of ¼ or less of a wavelength λ of a condensed light ray source to be radiated thereon;

means for cooling said reflecting mirror to a predetermined temperature;

a gas ejecting means for ejecting toward said reflecting mirror a gas to be measured;

means for projecting a condensed light ray onto a portion of said reflecting mirror against which said condensed light is projected so that dew and/or frost is formed;

means for detecting any sudden increase in the intensity of scattered light by electrostatic capacity of condensed moisture on said reflecting mirror and a thermocouple to measure said predetermined temperature of said reflecting mirror at said sudden increase in the intensity of scattered light, wherein said predetermined temperature corresponds to the dew point or frost point of the gas and said dew point or frost point is used to obtain a humidity value which corresponds to the amount of water in the gas.

9. An apparatus of claim 8, wherein said reflecting surface of the reflecting mirror is coated with an aluminum thin film.

10. An apparatus of claim 9, wherein said reflecting surface of the reflecting mirror is further coated with a protective film having good thermal conductivity, high hardness and high transparency.

11. An apparatus of claim 10, wherein said protective film is an aluminum nitride thin film.

12. An apparatus of claim 8 or 9 or 10, wherein said cooling means comprises a small-sized helium refrigerating machine.

13. An apparatus of claim 8 or 9 or 10, wherein said condensed light ray projecting means comprises a light-emitting diode.

14. An apparatus of claim 8 or 9 or 10, wherein said gas ejecting means comprises a heat resistant hydrophobic filter disposed at an inlet for the gas to be measured.

* * * * *